United States Patent
Unetich

(10) Patent No.: US 9,050,166 B2
(45) Date of Patent: Jun. 9, 2015

(54) COUPLING METHOD FOR RESONANT DIATHERMY AND OTHER BIO-TISSUE HEATING APPLICATORS

(75) Inventor: Robert M. Unetich, Pittsburgh, PA (US)

(73) Assignee: ReGear Life Sciences, Inc., Pittsburgh, PA (US)

( * ) Notice: Subject to any disclaimer, the term of this patent is extended or adjusted under 35 U.S.C. 154(b) by 576 days.

(21) Appl. No.: 13/429,565

(22) Filed: Mar. 26, 2012

(65) Prior Publication Data

US 2012/0265277 A1 Oct. 18, 2012

Related U.S. Application Data

(60) Provisional application No. 61/476,514, filed on Apr. 18, 2011.

(51) Int. Cl.

| | | |
|---|---|---|
| *A61F 2/00* | (2006.01) | |
| *A61F 7/00* | (2006.01) | |
| *A61N 2/02* | (2006.01) | |
| *A61N 5/00* | (2006.01) | |
| *A61B 18/12* | (2006.01) | |

(52) U.S. Cl.
CPC . *A61F 7/007* (2013.01); *A61N 5/00* (2013.01); *A61N 2/02* (2013.01); *A61B 18/1206* (2013.01)

(58) Field of Classification Search
CPC ............................ A61B 18/12; A61B 18/1206
USPC ........................................................ 607/101
See application file for complete search history.

(56) References Cited

U.S. PATENT DOCUMENTS

| | | | | |
|---|---|---|---|---|
| 3,747,013 A * | 7/1973 | Mettler | ............................ | 331/74 |
| 4,431,888 A | 2/1984 | Simpson | | |
| 4,638,813 A * | 1/1987 | Turner | ......................... | 607/154 |
| 4,685,462 A | 8/1987 | Olsen | | |
| 4,837,514 A | 6/1989 | Spies | | |
| 4,979,218 A | 12/1990 | Strahm | | |
| 4,996,484 A | 2/1991 | Spies | | |
| 5,160,828 A | 11/1992 | Olsen | | |
| 6,094,599 A * | 7/2000 | Bingham et al. | .............. | 607/149 |
| 6,221,094 B1 * | 4/2001 | Bare | .................... | 607/1 |
| 6,735,481 B1 * | 5/2004 | Bingham et al. | .............. | 607/149 |
| 6,853,337 B2 | 2/2005 | Barabash | | |
| 6,853,865 B2 * | 2/2005 | Beens et al. | ................... | 607/103 |
| 7,510,555 B2 * | 3/2009 | Kanzius | .......................... | 606/33 |
| 8,328,800 B2 * | 12/2012 | Brannan | ......................... | 606/41 |
| 2008/0215115 A1 * | 9/2008 | Bingham et al. | ................ | 607/48 |

* cited by examiner

*Primary Examiner* — Ronald Hupczey
*Assistant Examiner* — Noran Abraham
(74) *Attorney, Agent, or Firm* — The Webb Law Firm

(57) ABSTRACT

A diathermy apparatus includes a cylindrical coil (24) defining an opening (42), a pair of capacitors of substantially similar capacitance (20 and 22), each capacitor connected to one end of the coil, an RF signal source (26), and a balun (28) connected between the RF signal source (26) and the pair of capacitors (20 and 22). The balun (28) is operative for converting an unbalanced signal received from the RF signal source (26) into a balanced signal supplied to coil (24) via the pair of capacitors (20 and 22). Desirably, the cylindrical coil is a conical cylindrical (or cone-shaped) spiral coil.

7 Claims, 3 Drawing Sheets

COUPLING METHOD FOR RESONANT DIATHERMY AND OTHER BIO-TISSUE HEATING APPLICATORS

CROSS REFERENCE TO RELATED APPLICATIONS

The present application claims priority to U.S. Provisional Patent Application No. 61/476,514, filed Apr. 18, 2011, which is incorporated herein by reference.

BACKGROUND OF THE INVENTION

1. Technical Field

This invention relates to diathermic devices used for therapeutic heating and, in particular, to systems for administering the application of diathermic energy in a controlled way.

2. Background Art

Resonant-circuit diathermic devices used for therapeutic heating (as opposed to non-resonant devices which have been eclipsed) represent a growing market. These devices have the ability to provide accurate warming of body areas without heating the intervening skin. U.S. Pat. No. 4,685,462, for example, describes warming of the body in the treatment of severe hypothermia, wherein a victim may be warmed internally in order to minimize the risk of cardiac arrest or skin burns. U.S. Pat. No. 6,094,599 describes the use of such a device in a controlled medical or therapeutic environment, such as a series of therapy sessions, to provide deep warming of injured tissue to enhance the therapeutic effect of improved blood flow. U.S. Pat. No. 5,160,828 teaches the use of body-conforming garments for the purpose of precisely controlling the duration and location of heating application during therapeutic sessions.

With reference to FIG. 1, prior art resonant assemblies rely upon the use of two inductively-coupled coil assemblies 2 and 4. These assemblies typically include a first source-side inductive coil (or primary coil or winding) 6 which is driven by a tuned RF source 8 and inductively-coupled to a second patient-side inductive coil (or secondary coil or winding) 10 which acts as a resonant applicator. Coil assembly 4 may include a tuning device 12, such as a variable capacitor, that facilitates tuning of coil assembly 4 into resonance with coil assembly 2 when coil assembly 4 is positioned to apply therapeutic heating to a patient (not shown).

Inductive coupling is achieved by placing primary winding 6 near a portion of the tuned secondary winding 10. The patient-side inductive coil (or secondary winding) 10 is placed adjacent the source-side coil (or primary winding) 6 at a predetermined distance D from said source-side coil 6. Typically, the chosen distance D is some known small fraction of a wavelength in order to facilitate constructive wave induction such as is common in applications regarding the transfer of electromagnetic wave energy from one medium to another. The combination of the patient-side coil 10, together with the patient's body tissue and a suitable tuning device 12 (such as a variable capacitor), constitute a circuit. The variable capacitor 12 allows the resonant frequency of this circuit to be adjusted, or "tuned" to resonance for efficient delivery of power to the patient.

Careful placement of the coils 6 and 10 achieves desired coupling. By selecting an optimum turns ratio, the impedance of the tuned circuit (10, 12 and the patient's body tissue) can be transformed to a convenient value, such as 50 or 70 ohms, for connection to RF source 8.

However, the source-side coil 6 thus inductively coupled suffers from several disadvantages. For example, secondary coil 10 is required to encompass a body part such as an arm or leg and is therefore of minimum size. Being conductive because of its inductive properties, secondary coil 10 must also be made of metal wires, which add weight. The weight and size inherent to these requirements hampers mobility and flexibility, from the points of view of both the patient and the therapy administrator.

Moreover, the wire windings of secondary coil 10 are inherently sensitive to spacing. Specifically, the windings of secondary coil 10 are desirably constructed in a periodic way, that is to say that the distance between consecutive turns of the winding of secondary coil 10 is desirably kept as constant as possible at a predetermined separation distance for optimal power transfer as is known in the art.

Furthermore, in order to be used in a point-of-treatment environment, secondary coil 10 must be portable and operable by health personnel with no guaranteed knowledge of its internal electrical function.

Yet another disadvantage is the non-uniform distribution of magnetic field in the secondary coil assembly 10 due to the effects of induction. Still a further disadvantage is the incidental and undesired capacitive coupling between coils 6 and 10 which "unbalances" secondary coil assembly 4 by forcing the end of secondary coil 10 near primary coil 6 to be closer to the normally near ground potential of RF source 8.

While inductive coupling of coils 6 and 10 suggests that it is balanced since current flowing in secondary coil 10 is caused by current in primary coil 6 and not by the voltages present relative to ground by either end of primary coil 6, in reality inductive coupling of coils 6 and 10 is not well balanced. This is because there is substantial stray capacitive coupling from primary coil 6 to whatever portions of secondary coil 8 are located nearby, which stray capacitive coupling adds a current path from primary coil 6 to secondary coil 10.

If primary coil 6 is driven by an unbalanced shielded coaxial cable 30, as is normally the case, one end of primary coil 6 is connected to ground G (as shown in FIG. 1) and the other end is near ground potential because primary coil 6 represents a low impedance path to ground G.

U.S. Pat. No. 6,853,865 suggests adding a balanced transformer (a balun) before primary coil 6 to convert the drive signal to primary coil 6 to an unbalanced feed relative to ground. This has proven to be less than ideal in practice because building a balanced balun of sufficiently high output impedance, relative to the very high impedance of the resonant secondary coil 10, is not practical. It has also been suggested to place primary coil 6 at the center of secondary coil 10. This is also difficult to do because primary and/or secondary coils of diathermic applicators can take on an asymmetric shape(s). Furthermore, primary and/or secondary coils designed to conform to body part shapes, as is usually the case, are not perfect cylinders. Still further, the human body presents stray capacitances to ground, which make the physical center of the secondary coil an uncertain effective ground point. Furthermore, inductive coupling between primary and secondary coils suffers from being subject to subtle details of wire placement and it is difficult to retain this exact placement over time. Also, inductive coupling cannot be done in a well-balanced manner because of uncertainty of the virtual center of the secondary coil. The prior art has not identified the source of this problem.

In some ways unbalanced inductive coupling resembles the problem in the field of audio amplifiers of common-mode voltage caused by poor grounding leading to a 60-cycle hum. U.S. Pat. No. 4,979,218 teaches common-mode rejection to overcome poor grounding in audio amplifiers. However, audio amplifiers do not suffer from the same kind of unpredictable variation in output circuit dynamics since they do not radiate at frequencies sufficient to inadvertently incorporate surrounding objects into their resonant circuit.

Also, the problem of unbalanced inductive coupling cannot simply be solved by providing shielding, such as in the case of a microwave oven (U.S. Pat. No. 4,431,888) because the element being heated by the present invention (in this case the patient) has a path to ground which is not contained.

U.S. Pat. No. 4,996,484 teaches noise cancellation to remove power line noise from geophysical equipment, but requires the use of complicated electronics such as phase-locked loops. U.S. Pat. No. 4,837,514 teaches tracking and digitally removing noise.

However, neither the balun nor any other feature of the prior art is capable of overcoming the leakage problem due to the unintentional unbalancing of the secondary coil and attendant de-tuning of the entire resonant circuit unavoidably caused by the patient.

While capacitive coupling networks for signal transmission are generally known, capacitive coupling networks designed to overcome the unpredictable, adverse and stray capacitances that couple through leakage into a patient's body are not known in the prior art.

Consequently, there exists a need to provide a compact, robust system that stably applies tuned-power through a patient-side coil for the purposes of therapeutic treatment.

SUMMARY OF THE INVENTION

The present invention overcomes the problem in the art of resonant diathermic heating by disclosing a method and means for reliably and efficiently boosting the common-mode rejection ratio (CMRR) of the circuit driving the secondary coil. More specifically, the present invention provides a method and system which avoids the foregoing problems and others by eliminating inductive coupling. The present invention replaces inductive coupling with capacitive coupling done in a symmetrical manner to each end of the secondary winding.

Diathermic circuits do exist to reduce common-mode voltage with a balun, such as the equivalent resonant circuits disclosed in U.S. Pat. Nos. 6,094,599 and 6,853,865. However, unintentional capacitive coupling on the secondary coil (due to motion or other interaction of the treatment recipient) is not effectively prevented from adversely affecting the characteristics of the equivalent resonant circuit.

A typical secondary coil of the applications intended for the present invention and its body-conforming garment has the shape of a conical cylinder. In cross-section, such typical secondary coil resembles somewhat the Archimedean spiral of the prior art (e.g., U.S. Pat. Nos. 6,094,599 and 6,853,865) but also extends a substantial distance in a third dimension, namely, a longitudinal axis of a conical (or cone-shaped) cylinder.

For the case of a symmetrical, balanced secondary coil, as is desirable in order to reject the common mode as much as possible, the effective ground point is assumed to be situated somewhere along the wire close to the middle of its longitudinal axis (if the wire were stretched out) but cannot be relied upon to adopt a fixed point. Consequently, the ground point exhibits a kind of spiral- and cylindrical-based parametric wandering. Any point below this ground point in voltage is thus free to couple RF energy back through the ground of the generator, which cannot be relied upon to be effective at diathermic treatment frequencies, into building electrical systems in contravention of established building codes.

In fact, the effective ground point in the secondary coil may arbitrarily drift as a result between the outer radius of the conical cylinder and its most central point (seen in cross-section). The prior art has no recourse but to persuade the diathermic treatment patient to maintain an absolutely fixed posture for the duration of the diathermic treatment, which is not likely given the usual duration of hours or fractions thereof.

In fact, in a preferred arrangement of the present invention, the conical cylinder is further complicated in shape to conform to applications of diathermy for treatment of the shoulder region of a patient. In this case the drifting of the effective ground point may be expected to generalize from the wandering mentioned above to even less predictable patterns. The unbalancing of the secondary coil and the attendant building code violations, which prevent the device from ever achieving FCC approval for household use, are thus even more extreme.

As a further feature, the present invention teaches the application of a balun in such a way that the driving device is free to adopt a ground point in whatever manner is dictated by the circumstances, without causing penalties in stray conducted radiation, which is not taught by the prior art.

As a further feature of the present invention, capacitors are used to establish the needed coupling. Capacitors have the advantage, as is known in the art, that as passive devices they can be specified accurately and remain stable over time.

Also, as discussed above, the effective ground of the secondary coil cannot be guaranteed to be situated half-way through the turns.

As will be described in greater detail below, some aspects of the problem solved by the present invention resemble the problems faced by designers in the art of broadcast antennas, such as is taught in U.S. Pat. No. 6,853,337. However, broadcast antennas have a remedy that is not available to the present invention, in that they typically are not forced to transceive in such close proximity to large bodies of highly-electrodynamically absorbing materials. Furthermore, broadcast antennas do not face the complication that such bodies present modifications to the effective circuit topology of the output stage whose characteristics vary nonlinearly and temporally, like stray capacitances and such.

Therefore, as can be seen by a person of skill in the art, the benefits of the balun by itself are not sufficient to overcome the additional problems presented by the art of resonant diathermy.

Further, inductive coupling suffers from having cancellation of magnetic fields near the point of maximum coupling, making the use of the coil as a heat applicator to tissue non-uniform. Capacitive coupling overcomes this disadvantage because it has completely symmetrical field distributions.

More specifically, the present invention is a diathermy apparatus comprising: a cylindrical coil 24 defining an opening 42; a pair of capacitors of substantially similar capacitance 20 and 22, each capacitor connected to one end of the coil 24; an RF signal source 26; and a balun 28 connected between the RF signal source 26 and the pair of capacitors 20 and 22, said balun 28 operative for converting an unbalanced signal received from the RF signal source 26 into a balanced signal supplied to coil 24 via the pair of capacitors 20 and 22.

The diathermy apparatus can include a co-axial cable 30 connecting the RF signal source and the balun. The balun can be operative for converting the unbalanced signal received from the RF signal source via the co-axial cable 30 into the balanced signal supplied to the coil via the pair of capacitors.

An impedance matching circuit can be provided between the RF signal source and the balun. An adjustable capacitor 36 can be in parallel with the coil 24, which can be disposed on a substrate or garment.

The opening 42 can be adapted to receive a body part.

The cylindrical coil can be a conical cylindrical (or cone-shaped) spiral coil.

The invention is also a diathermy apparatus comprising: a cylindrical coil 24 having a first end and a second end; a first capacitor 20 connected to the first end of the coil 24; a second capacitor 22 connected to the second end of the coil 24; a balun connected to the first capacitor 20 via a first lead 32, said balun connected to the second capacitor 22 via a second lead 34; and an RF signal source operative for supplying an unbalanced signal to the balun which converts the unbalanced signal into a balanced signal which the balun outputs on the first and second leads 32 and 34.

The cylindrical coil can be a conical cylindrical (or cone-shaped) spiral coil. The first and second capacitors can have the same or substantially the same values. A support substrate can be coupled to the coil. The coil can define an opening adapted to receive a body part.

An impedance matching network can be coupled between the RF signal source and the balun.

In response to the RF signal source outputting an RF signal, each capacitor can have impressed thereon about 500 Vac, and the coil can have impressed thereon about 1000 Vac.

The diathermy apparatus can further include an adjustable capacitor 36 in parallel with the coil 24.

Lastly, the invention is an RF diathermy treatment method comprising: (a) converting an unbalanced input RF signal into a balanced RF signal output on first and second wires 32 and 34; (b) applying the balanced RF signal output on the first wire 32 to a first end of a cylindrical coil 24 positioned about a body part of a patient via a first capacitor 20; and (c) applying the balanced RF signal output on the second wire 34 to a second end of the cylindrical coil 24 via a second, similar or substantially similar capacitor 22.

The cylindrical coil 24 can be a conical cylindrical (or cone-shaped) spiral coil.

The body part of the patient can be received in an opening of the cylindrical coil 24 that is adapted to receive the body part of the patient.

The cylindrical coil 24 can be disposed on a support substrate.

An adjustable capacitor can be electrically coupled in parallel with the cylindrical coil 24.

DETAILED DESCRIPTION OF THE INVENTION

Figure 1:
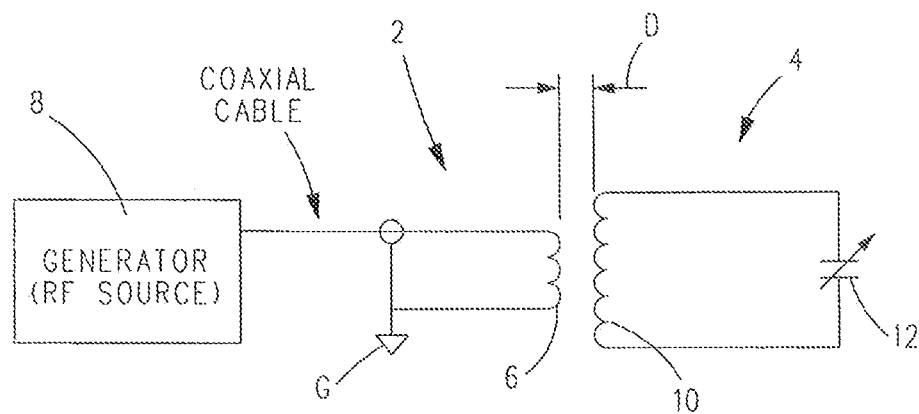
FIG. 1 is a schematic diagram showing a typical coupling network of a prior art doubled-coil diathermy apparatus.

The present invention will now be described with reference to the accompanying figures where like reference numerals correspond to like elements.

Figure 2:
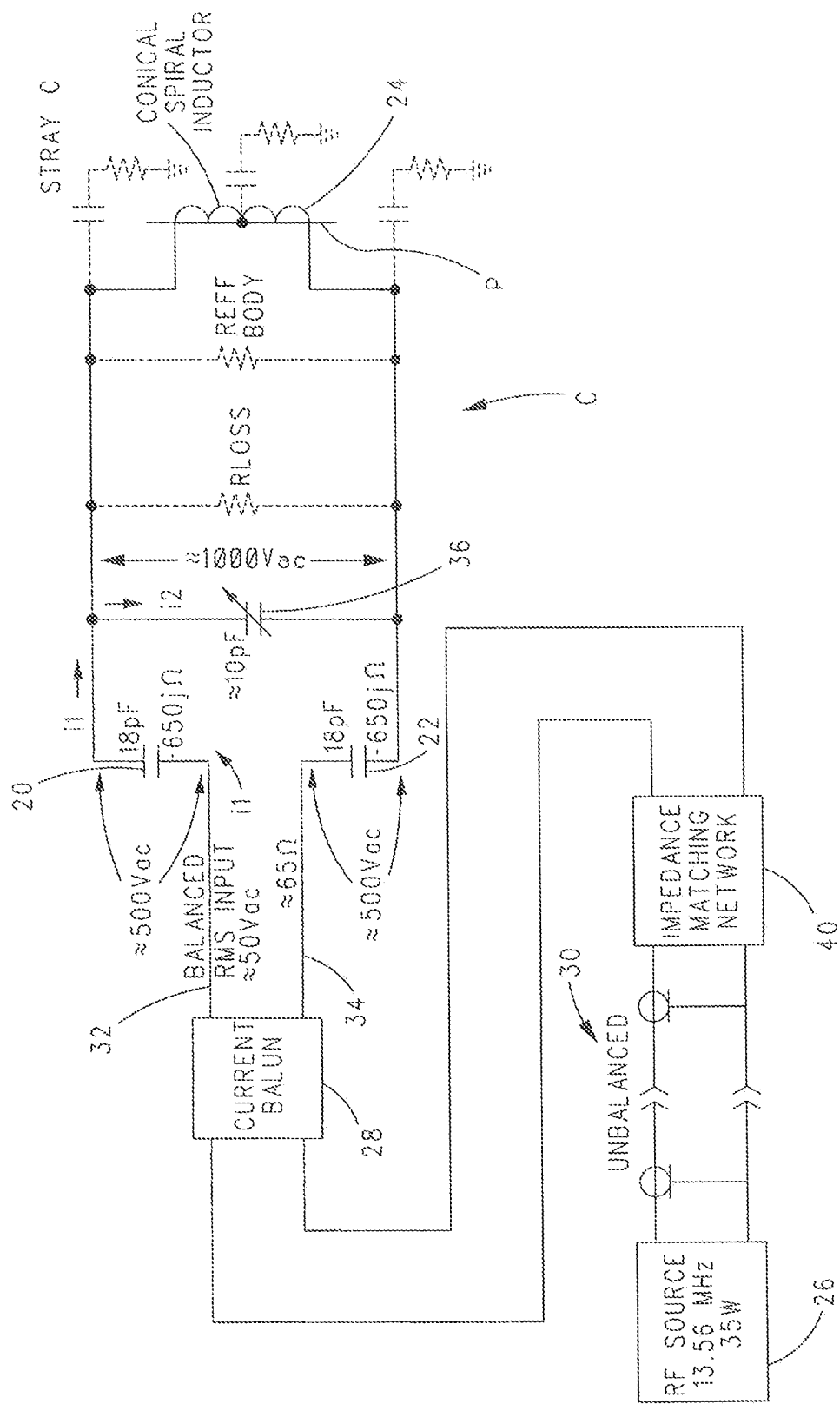
FIGS. 2 and 3 are diagrams showing a capacitively-coupled diathermy apparatus according to the present invention.

With reference to FIG. 2, in the present invention, capacitive coupling with two identical (or substantially identical) capacitors 20 and 22 is used to achieve symmetrical (or substantially symmetrical) coupling to each end of a circuit C, comprised of a conical cylindrical (or cone-shaped) spiral coil 24 and an optional parallel tuning capacitor 36, that is utilized for the application of RF diathermy treatment to a patient P. The present invention relies on the specific values of capacitors 20 and 22 to achieve the capacitive coupling desired.

Capacitive coupling is done in a manner symmetrical to each end of coil 24. The values of coupling capacitors 20 and 22 can be selected to achieve the desired coupling and since they are electrically symmetrically placed, the voltage across each capacitor 20 and 22 is identical (or substantially identical), greatly reducing common-mode voltages between an RF signal source 26 and coil 24, wherein common-mode voltages, as opposed to differential-mode voltages, being undesirable are reduced or eliminated by a balun 28 disposed in a path of RF current between RF source 26 and coil 24 and a very large reactance to ground realized by capacitive-coupling to the skin of a patient (the patient is shown schematically in FIG. 2 by line P).

Balun 28 receives unbalanced driving current from RF source 26, for example, via a co-axial cable 30 and an optional impedance matching network 40, which can be adapted to match (or substantially match) the input impedance of balun 28 to the output impedance of RF source 26 and co-axial cable 30 seen by impedance matching network 40. This driving current is considered unbalanced because it oscillates about some effective ground potential G that changes little over time, if at all. The driving current is supplied through co-axial cable 30 and optional impedance matching network 40 by RF source 26 to balun 28 which, through use of the transforming aspects of balun 28, removes the effective ground potential G.

This causes current output by balun 28 on leads 32 and 34 to oscillate between said leads 32 and 34 independent of ground potential. The advantage created by balun 28, for purposes of this invention, is that a balanced output voltage of balun 28 is desirable in order to minimize, to the extent possible, wasted power which leaks into intended or unintended receiving matter, either electrodynamically or non-electrodynamically. The same need for a balanced output is true in the case of an antenna transceiver, as is known in the non-analogous art of broadcasting. In particular, the present invention identifies the further problem, inherent to its proper native art, that RF energy can inadvertently be sunk into nearby ground-loops, causing power-wastage and problems in an entire distribution network, a consequence which is an express barrier to FCC approval of resonant diathermic devices and the like for home use.

As was mentioned above, the benefits of balun 28 by itself are not sufficient to overcome the additional problems presented by the art of resonant diathermy.

Figure 4:
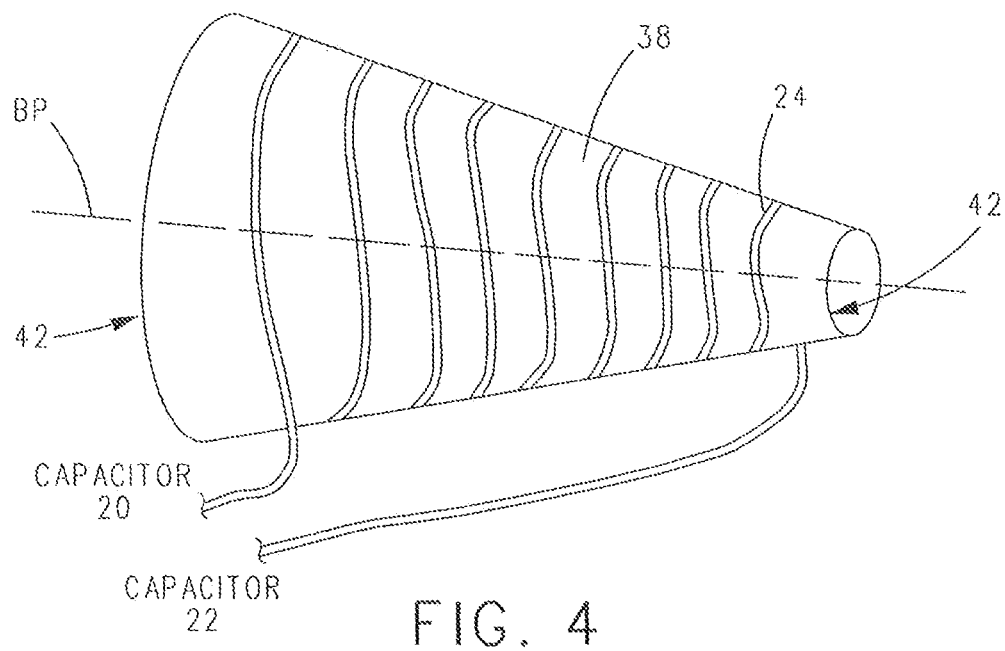
FIG. 4 is an isolated perspective view of the conical (cone) shaped secondary coil shown in FIGS. 2 and 3 disposed on a truncated cone-shaped support substrate or garment.

The present invention capitalizes in a novel way on the above-mentioned properties of balun 28 by allowing the effective ground point of coil 24 to drift somewhat in response to natural variation in the position of the patient wearing coil 24, either alone or disposed on a support substrate 38, such as a wearable garment (FIG. 4), or other incidental surrounding objects which may inadvertently become part of or coupled to circuit C during the course of diathermic treatment. Conical spiral coil 28 and substrate 38, (if provided), define along a longitudinal axis thereof an opening 42 of coil 28, the size of which is adapted to receiving a body part BP of a patient during diathermy treatment. When support substrate 38 is provided, coil 28 can be affixed to and supported by substrate 38, which can also have a generally conical shape that matches the shape of conical spiral coil 24 or which facilitate coil 24 having a conical spiral shape.

Figure 3:
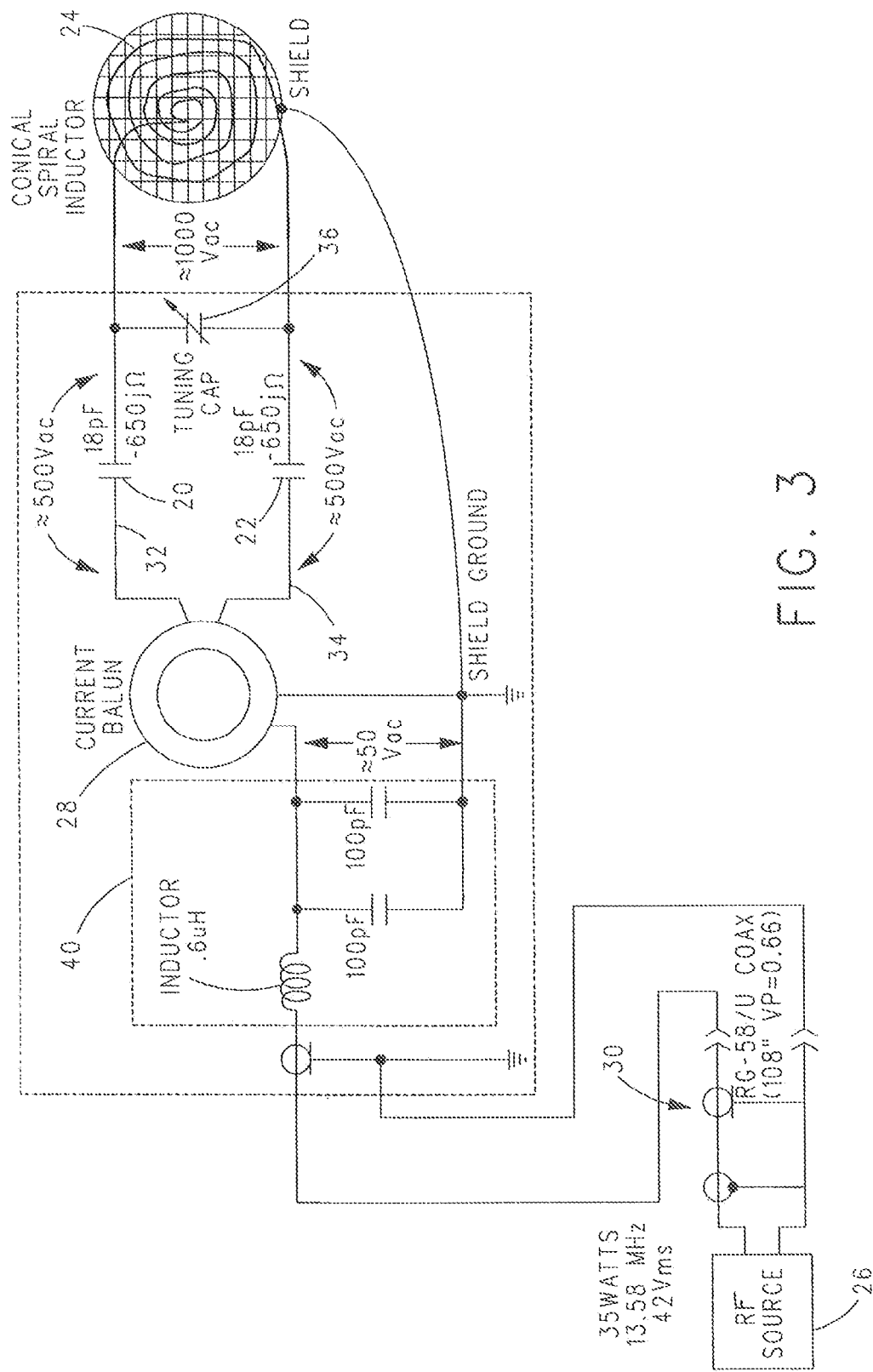

With reference to FIG. 3 and with continuing reference to FIG. 2, a further advantage of the present method will now be described. As mentioned above, capacitive coupling via capacitors 20 and 22 overcomes the cancellation of magnetic fields near the point of maximum coupling, thereby enabling coil 24 to apply uniform heat to a patient's tissue because coil 24 has completely (or substantially completely) symmetrical field distributions. Although the effective ground point of coil 24 may wander from one end of coil 24 to another in response to transient stray capacitances constantly created and destroyed by shifting of the patient's posture and other factors, the driving voltage recovers with no change in the performance of coil 24. Furthermore, the adverse effects of unbalancing coil 24 are greatly reduced, allowing predictable constant warming to be delivered to appropriate areas with minimal waste and minimal ground-loop disruption of circuitry C.

Use of capacitors 20 and 22 eliminates the problems associated with the two-winding inductive method shown in FIG. 1. Another advantage is that capacitors 20 and 22 are passive elements that rely entirely on their specific capacitor values to achieve the capacitive coupling desired.

For example, without limitation, the 18 pF capacitors shown in FIG. 3, with a reactance of approximately $-700\,j\Omega$ ($-650\,j\Omega$ in FIG. 3) have an impedance at the driving frequency of RF signal source 26 which, in the 25 meter band usually used for diathermy application is about 13 or 14 MHz, takes 40 or so watts from the output of balun 28.

The current output by balun 28, which is approximately 0.7 Amps, symmetrically produces about 500 volts across each coupling capacitor 20 and 22, which thereby produces approximately 1 kV at the input to coil 24, as can be easily verified empirically. Such a voltage is ideal for diathermic heating.

By using balun 28 to establish a balanced feed (or drive signals) to two equal (or substantially equal) value capacitors 20 and 22 (without limitation, 18 pF capacitors in this example) connected to the ends of coil 24, circuit C is naturally in balance and floating relative to actual ground potential. Thus, a patient's body part inserted in opening 42 of coil 24 may be grounded by stray capacitance to ground or it may be floating relative to ground with no change in the performance of coil 24 to heat the patient's body part.

The invention has been described with reference to an exemplary embodiment. Obvious modifications and alterations will occur to others upon reading and understanding the preceding detailed description. It is intended that the invention be construed as including all such modifications and alterations insofar as they come within the scope of the appended claims or the equivalents thereof.

The invention claimed is:

1. A diathermy apparatus comprising:
   a cylindrical coil (24) having a first end and a second end;
   a first capacitor (20) connected to the first end of the coil (24);
   a second capacitor (22) connected to the second end of the coil (24);
   a balun connected to the first capacitor (20) via a first lead (32), said balun connected to the second capacitor (22) via a second lead (34); and
   an RF signal source operative for supplying an unbalanced signal to the balun which converts the unbalanced signal into a balanced signal which the balun outputs on the first and second leads (32 and 34);
   wherein, in response to the RF signal source outputting an RF signal, each capacitor has impressed thereon about 500 Vac, whereupon the coil has impressed thereon about 1000 Vac.

2. The diathermy apparatus of claim 1, wherein the cylindrical coil is a conical cylindrical or cone-shaped spiral coil.

3. The diathermy apparatus of claim 1, wherein the first and second capacitors have the same or substantially the same values.

4. The diathermy apparatus of claim 1, wherein the coil is coupled to a support.

5. The diathermy apparatus of claim 1, wherein the coil defines an opening adapted to receive a body part.

6. The diathermy apparatus of claim 1, further including an impedance matching network between the RF signal source and the balun.

7. The diathermy apparatus of claim 1, further including an adjustable capacitor (36) in parallel with the coil (24).

* * * * *